United States Patent [19]

Erben

[11] 4,184,361
[45] Jan. 22, 1980

[54] SLIVER DENSITY SENSING APPARATUS

[75] Inventor: Ludwig Erben, Mönchen-Gladbach, Fed. Rep. of Germany

[73] Assignee: Trützschler GmbH & Co. KG, Mönchen-Gladbach, Fed. Rep. of Germany

[21] Appl. No.: 862,825

[22] Filed: Dec. 16, 1977

[30] Foreign Application Priority Data

Dec. 18, 1976 [DE] Fed. Rep. of Germany ....... 2657603

[51] Int. Cl.² .................. D01G 23/06; D01H 5/38; G01N 9/26; G01B 13/00
[52] U.S. Cl. ........................ 73/37.7; 19/240; 73/160
[58] Field of Search .............. 73/37.5–37.8, 73/160; 19/239, 240

[56] References Cited

U.S. PATENT DOCUMENTS

| | | | |
|---|---|---|---|
| 2,843,882 | 7/1958 | Lewis et al. | 73/37.7 X |
| 3,154,810 | 11/1964 | Horne | 73/37.7 X |
| 3,411,352 | 11/1968 | Stoller | 73/37.7 X |
| 3,435,673 | 4/1969 | Felix | 73/37.7 X |
| 3,485,095 | 12/1969 | Hirata et al. | 73/37.7 X |
| 3,710,421 | 1/1973 | Tooka | 73/37.7 X |
| 3,722,260 | 3/1973 | Staheli | 73/37.7 |
| 3,752,170 | 8/1973 | Murbach | 73/37.7 X |
| 3,854,330 | 12/1974 | Wildbolz | 73/37.7 X |
| 4,075,739 | 2/1978 | Staheli | 73/37.7 X |

Primary Examiner—John Petrakes
Attorney, Agent, or Firm—Spencer & Kaye

[57] ABSTRACT

An apparatus for sensing the density variation of a sliver, includes a sliver funnel through which the sliver passes and which has an intake portion, a discharge portion and a chamber formed as an enlarged part of the discharge portion. The chamber is, through a lateral opening, in communication with a source of pressurized air and a pressure sensing device. The pressure sensing device receives pneumatic signals as a function of the variation of pressure in the chamber dependent upon the density of the sliver portion momentarily present in the chamber. The sliver funnel is arranged at an output of a carding machine for receiving a web discharged thereby and for combining the web into a sliver passing through the chamber. The pressure sensing device comprises a pressure-responsive precision sensor which includes an arrangement for converting the pneumatic signals into digital signals.

10 Claims, 4 Drawing Figures

SLIVER DENSITY SENSING APPARATUS

BACKGROUND OF THE INVENTION

This invention relates to an apparatus for sensing the density variations of a textile sliver and is of the type that has a sliver funnel which combines a running web into a sliver which passes through a pressure chamber provided in the discharge portion of the sliver funnel. The pressure chamber has a lateral opening through which compressed air is supplied from a pressure source. The lateral opening further communicates with a pressure-responsive sensor which responds to pressure fluctuations in the pressure chamber, caused by density fluctuations of the sliver passing through the pressure chamber. Such pressure fluctuations are generated because, dependent upon the density of the sliver portion of the running sliver momentarily present in the pressure chamber, the air quantities absorbed by the sliver vary, thus causing alteration of the pressure in the pressure chamber. The pressure-responsive sensor generates a signal as a function of the fluctuation of the sliver density; this signal can be utilized to alter the sliver density.

A sliver control of the above-outlined type is disclosed, for example, in Lothar Simon, *Pneumatische Messwertaufnahme in der Spinnereivorbereitung* (Pneumatic Measurement Sensing for the Preparation of Spinning), TEXTILTECHNIK, Vol. 25, 1975, Issue 12, pages 759–764. According to this publication, the fluctuations of the pressure prevailing in the pressure chamber of a measuring nozzle (sliver funnel) are sensed by a diaphragm-type pressure-responsive sensor which generates an analog signal by affecting a lever arrangement which, in turn, cooperates with a resistance of an electric bridge circuit. The analog signal is applied to a web stretching machine for varying the cross section of the web introduced into the sliver funnel from the output of the web stretching machine.

SUMMARY OF THE INVENTION

It is an object of the invention to provide a more accurate sensing of the density variations of the running sliver, particularly for the purpose of a more advantageous regulation of the sliver for ensuring more uniform cross-sectional properties throughout its running length.

This object and others to become apparent as the specification progresses, are accomplished by the invention, according to which, briefly stated, the sliver funnel which, in its discharge portion has a pressure chamber through which the sliver passes, is arranged at the outlet of a carding machine and the pressure chamber is in communication with a pressure-responsive precision sensor which converts the pneumatic signals into digital signals. The digital signals can subsequently be applied to the carding machine to alter the output rate of the textile web.

DESCRIPTION OF THE PREFERRED EMBODIMENT

Figure 1:
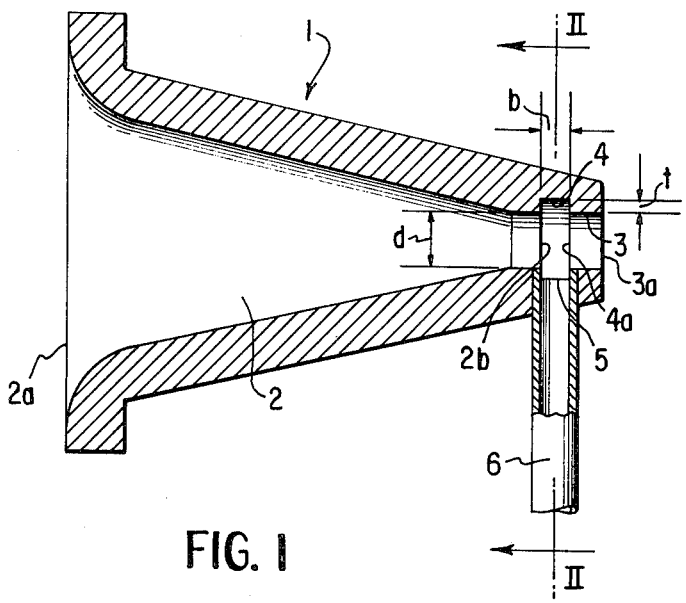
FIG. 1 is an axial sectional view of a sliver funnel advantageously incorporated in the apparatus according to the invention.
Figure 2:
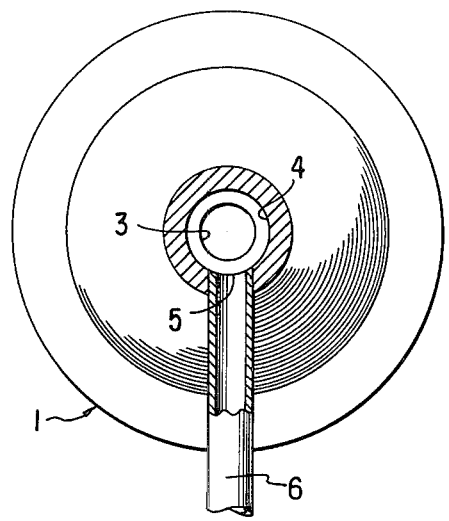
FIG. 2 is a sectional view taken along line II–II of FIG. 1.

Turning now to FIGS. 1 and 2, the sliver forming and measuring funnel 1 shown therein has a conical intake portion 2 which has a relatively large-diameter inlet opening 2a and an outlet opening 2b, the relatively small diameter of which is designated with d. The intake portion 2 continues in a discharge portion 3, the axially viewed length of which is smaller than that of the intake portion 2. The discharge portion 3 has an outlet opening 3a.

The initial part of the discharge portion 3 is enlarged to constitute a cylindrical cavity forming a pessure chamber 4. As it can be seen in FIG. 1, the pressure chamber inlet is constituted by the outlet opening 2b of the intake portion 2, while the pressure chamber outlet is designated at 4a. The pressure chamber 4 has an axially measured length b and a radially measured depth t.

The pressure chamber 4 is provided with a lateral opening 5.

Figure 3:
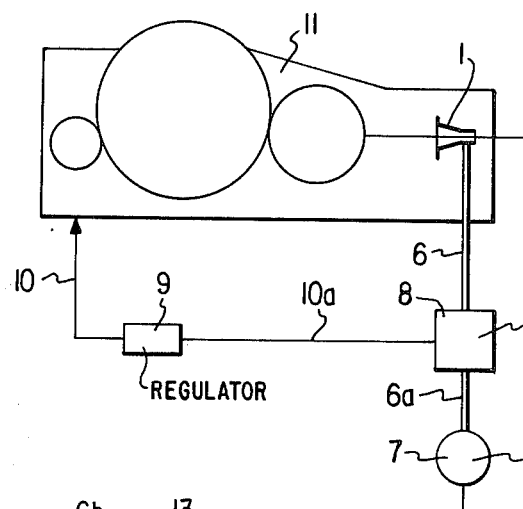
FIG. 3 is a block diagram of a preferred embodiment of the invention.

FIG. 3 shows a sliver which passes through the sliver funnel 1 after the carding machine 11. The sliver funnel 1 is connected with the air pressure-responsive switch 8 by means of the conduit 6. The air pressure-responsive switch 8 is connected to an air pressure source 7 by means of the conduit 6a. Further, the air pressure-responsive switch 8 is connected by means of an electric conductor 10a with a regulator 9, known by itself. The regulator 9 is connected by means of an electric conductor 10 with the carding machine 11 or with a tuft depositing shaft (not shown) coupled to the carding machine and situated upstream thereof. The analog pneumatic signal which affects the air pressure-responsive precision switch 8 is converted into a digital electric signal in the air pressure-responsive switch 8. This digital electric signal is applied to the regulator 9 as an input signal. The output signal of the regulator 9 controls a setting member which is known by itself and which is arranged at the carding machine 11 or at the tuft depositing shaft connected to the carding machine upstream thereof. In this manner, the quantity of the fiber material fed to the sliver funnel 1 can be varied.

Figure 4:
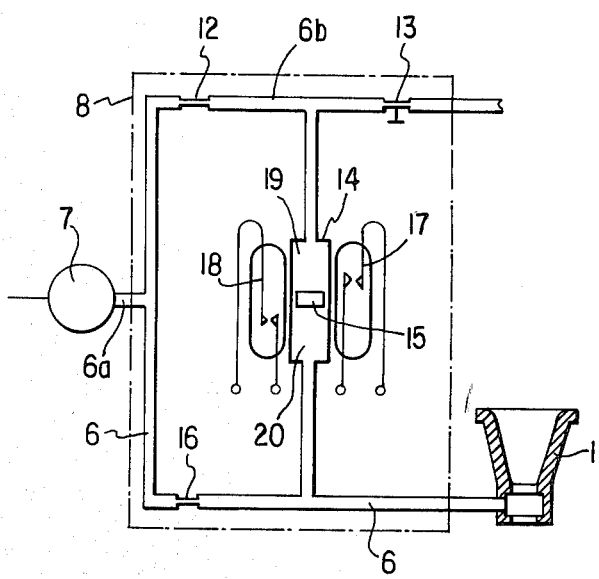
FIG. 4 is a schematic plan view of details of a component shown in FIG. 3.

FIG. 4 illustrates the air pressure-responsive precision switch 8, known by itself. From the air pressure source 7 a feeding pressure of, for example, 2 bars enters the air pressure-responsive switch 8 via the conduit 6a. The conduit 6a branches off into conduits 6 and 6b. The conduit 6b is connected with the ambient atmosphere through a throttle 12 and an adjustable nozzle 13. The conduit 6b is connected with one side of a receptacle 14 by means of a branch conduit extending from between the throttle 12 and the adjustable nozzle 13. In the receptacle 14 there is arranged an easily displaceable magnetic piston 15 which divides the receptacle 14 into two chambers 19 and 20. The conduit 6 leads to the sliver funnel 1 through a throttle 16. The conduit 6 is connected with the other side of the receptacle 14 by means of a branch conduit extending from between the throttle 16 and the sliver funnel 1. Two spring leaf contacts 17 and 18 are arranged parallel to the magnetic piston 15 and are connected with the regulator (not shown). The analog pneumatic signal which is obtained as a back pressure from the conduit 6 of the sliver funnel 1, enters the chamber 20 of the receptacle 14 and affects the magnetic piston 15. Upon exceeding or falling below a predetermined tolerance range for the thickness of the sliver, the respective spring leaf contact 17 or 18 closes and in this manner a digital electric signal is applied to the regulator.

These digital signals delivered by the requestor 9 are thus applied, by means of the conductor 10, to the carding machine 11 for varying, for example, the web output rate in response to the digital signals. The sliver forming and measuring funnel 1 is arranged at the output of the carding machine to thus receive the web discharged therefrom.

During operation, the web formed and discharged by the carding machine 11 enters the inlet opening 2a of the intake portion 2 and is combined to form a sliver having a diameter d which corresponds to that of the outlet opening 2b of the intake portion 2. Thus, while the sliver firmly lies against the wall defining the outlet opening 2b, it passes through a free space of the pressure chamber 4 whose diameter is $d+2t$. The pressurized air stream, entering laterally into the pressure chamber 4 from the air pressure source 7 through the conduit 6, in part penetrates into the sliver and is carried out through the discharge portion 3 as the sliver leaves the sliver forming and measuring funnel 1. In case the density of the sliver varies, the air quantity that enters and is absorbed by the sliver also varies. In this manner, pressure fluctuations are generated which, in turn, are sensed by the pressure-responsive precision sensor 8. For increasing the surface area of the sliver within the pressure chamber 4 with respect to the free space between the sliver and the chamber wall (for increasing the relative pressure fluctuations in the chamber 4), the axially measured length b of the pressure chamber 4 is greater that its depth t. Further, the chamber length b and/or the chamber depth t is smaller than the diameter d of the intake outlet opening 2b in order to effect an operation with small air quantities and small pressures. By providing that the cross-sectional area of the chamber inlet 2b equals that of the chamber outlet 4a, it is ensured that the counterpressure built up by the air quantities entrained by the sliver remain the same. Further, to increase the sensitivity, the greatest dimension of the lateral opening 5 is smaller than the diameter d of the outlet opening 2b of the intake portion 2.

It will be understood that the above description of the present invention is susceptible to various modifications, changes and adaptations, and the same are intended to be comprehended within the meaning and range of equivalents of the appended claims.

What is claimed is:

1. An apparatus for sensing the density variation of a sliver, including a sliver funnel through which the sliver passes and which has an intake portion including an outlet opening having a diameter, a discharge portion adjoining the outlet opening of the intake portion and a chamber formed as an enlarged part of the discharge portion; the chamber having an inlet, an outlet and a lateral opening; the chamber being in communication with a source of pressurized air and a pressure sensing device through the lateral opening; the pressure sensing device receiving pneumatic signals as a function of the variation of pressure in the chamber dependent upon the density of the sliver portion momentarily present in the chamber; the improvement wherein said sliver funnel is arranged at an output of a carding machine for receiving a web discharged thereby and for combining it into a sliver passing through said chamber; said pressure sensing device comprising a pressure-responsive precision sensor including converter means for converting said pneumatic signals into digital signals; said converter means including means for emitting a first digital signal when the pneumatic signal exceeds a maximum predetermined value and means for emitting a second digital signal when the pneumatic signal falls below a minimum predetermined value; the value range between said maximum and minimum values representing a predetermined tolerance range of the density variation of the sliver.

2. An apparatus as defined in claim 1, further comprising means for applying said digital signals to said carding machine for varying the output thereof as a function of said digital signal.

3. An apparatus as defined in claim 1, wherein the cross-sectional area of the chamber inlet equals to that of the chamber outlet.

4. An apparatus as defined in claim 1, wherein the largest dimension of said lateral opening is smaller than the diameter of said outlet opening of said intake portion.

5. An apparatus as defined in claim 1, wherein said chamber has a cylindrical configuration.

6. An apparatus as defined in claim 1, wherein said chamber has an axially measured length and a radially measured depth; said length being greater than said depth.

7. An apparatus as defined in claim 1, wherein said chamber has an axially measured length; said length being smaller than said diameter of said outlet opening.

8. An apparatus as defined in claim 1, wherein said chamber has a radially measured depth; said depth being smaller than said diameter of said outlet opening.

9. An apparatus as defined in claim 1, wherein said discharge portion has an outlet opening; said discharge portion having a cylindrical configuration from the outlet of said chamber to the outlet opening of said discharge portion.

10. An apparatus as defined in claim 1, wherein the axially measured length of said discharge portion is smaller than the axially measured length of said intake portion.

* * * * *